(12) United States Patent
Gill et al.

(10) Patent No.: US 10,996,163 B1
(45) Date of Patent: May 4, 2021

(54) ACOUSTICALLY ISOLATED THERMOACOUSTIC IMAGING PROBE AND PROCESS OF MANUFACTURE

(71) Applicant: ENDRA Life Sciences Inc., Ann Arbor, MI (US)

(72) Inventors: Jeremy Gill, London (CA); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 0 days.

(21) Appl. No.: 17/146,773

(22) Filed: Jan. 12, 2021

(51) Int. Cl.
*G01N 21/17* (2006.01)
*A61B 5/00* (2006.01)
(Continued)

(52) U.S. Cl.
CPC ....... *G01N 21/1702* (2013.01); *A61B 5/0095* (2013.01); *A61B 8/4444* (2013.01); *G01N 22/00* (2013.01); *G01N 29/226* (2013.01); *G01N 29/2418* (2013.01); *G01N 29/2431* (2013.01); *G01N 29/32* (2013.01); *A61B 2560/0431* (2013.01); *G01H 1/00* (2013.01); *G01N 29/245* (2013.01); *G01N 29/265* (2013.01); *G01N 2021/1706* (2013.01); *G01N 2021/1708* (2013.01); *G01N 2291/02881* (2013.01); *G01N 2291/101* (2013.01)

(58) Field of Classification Search
CPC .......... A61B 5/0095; A61B 2560/0431; G01N 29/2418; G01N 29/2431; G01N 29/2425; G01N 29/32; G01N 29/226; G01N 29/265; G01N 29/245; G01N 2021/1704–1708; G01N 2021/1708; G01N 2021/1706; G01N 22/00; G01N 2291/02881; G01N 2291/101; G01H 1/00
USPC ....................................................... 73/24.02
See application file for complete search history.

(56) References Cited

U.S. PATENT DOCUMENTS 5,052,227 A * 10/1991 Le Floc'H ........... G01N 29/075
73/644
5,392,652 A * 2/1995 Levesque ............. G01N 29/043
73/629

(Continued)

*Primary Examiner* — David L Singer
(74) *Attorney, Agent, or Firm* — Stanley E. Jelic

(57) ABSTRACT

A thermoacoustic probe with an electromagnetic (EM) energy applicator, a thermoacoustic transducer, and a housing containing the applicator and thermoacoustic transducer and enabling an EM exit window and a transducer front face to be held flush with respect to each other. A first acoustic absorbing material is placed between the EM applicator and the transducer, between the EM applicator and the housing, and between the transducer and the housing as spacers; and a second acoustic absorbing material is injected between the EM applicator and the transducer, between the EM applicator and the housing, and between the transducer and the housing in the spaced gaps, wherein the first acoustic absorbing material and the second acoustic absorbing material are combined to form a sleeve covering the applicator sides and the transducer sides. The acoustic absorbing materials mitigate sound artifacts and noise resulting in cleaner signal data. In a preferred embodiment the applicator is a radio-frequency applicator, the transducer is a piezoelectric transducer, and the probe is utilizable for tissue imaging.

20 Claims, 4 Drawing Sheets

(51) Int. Cl.
*G01N 22/00* (2006.01)
*G01N 29/24* (2006.01)
*G01N 29/22* (2006.01)
*G01N 29/32* (2006.01)
*A61B 8/00* (2006.01)
*G01N 29/265* (2006.01)
*G01H 1/00* (2006.01)

(56) References Cited

U.S. PATENT DOCUMENTS

| | | | |
|---|---|---|---|
| 2002/0045819 A1* | 4/2002 | Garlick | G01N 29/0663 |
| | | | 600/437 |
| 2011/0031059 A1* | 2/2011 | Parish | A61F 11/08 |
| | | | 181/129 |
| 2011/0308317 A1* | 12/2011 | Mueller | H01L 41/23 |
| | | | 73/632 |
| 2013/0301380 A1* | 11/2013 | Oraevsky | A61B 8/5261 |
| | | | 367/7 |
| 2014/0039293 A1* | 2/2014 | Oraevsky | A61B 5/14552 |
| | | | 600/407 |
| 2014/0306579 A1* | 10/2014 | Weber | B06B 1/06 |
| | | | 310/337 |
| 2017/0032519 A1* | 2/2017 | Thornton | G01S 7/52049 |
| 2017/0332916 A1* | 11/2017 | Zalev | A61B 5/0095 |
| 2018/0206826 A1* | 7/2018 | Thornton | A61B 5/0095 |
| 2019/0038220 A1* | 2/2019 | Rubin | A61B 8/5223 |
| 2019/0150749 A1* | 5/2019 | Harris | A61B 5/0095 |
| 2019/0247012 A1* | 8/2019 | Belanger | A61B 5/0095 |
| 2019/0247014 A1* | 8/2019 | Belanger | A61B 8/4416 |
| 2019/0275562 A1* | 9/2019 | Thornton | G01N 29/32 |

* cited by examiner

ACOUSTICALLY ISOLATED THERMOACOUSTIC IMAGING PROBE AND PROCESS OF MANUFACTURE

FIELD

The subject disclosure relates to thermoacoustic imaging. In particular, the disclosure describes an acoustically isolated thermoacoustic imaging probe within a system and process of manufacture.

BACKGROUND

Thermoacoustic imaging is an imaging modality that provides information relating to the thermoelastic properties of tissue. Thermoacoustic imaging uses short pulses of electromagnetic energy, such as radio frequency (RF) pulses, directed into a subject to heat absorbing features within the subject rapidly, which in turn induces acoustic pressure waves that are detected using acoustic receivers, such as one or more thermoacoustic or ultrasound transducer arrays. The detected acoustic pressure waves are analyzed through signal processing and processed for presentation as thermoacoustic images that can be interpreted by an operator.

SUMMARY

The RF pulses can impact the acoustic receivers, either directly or indirectly, and create sound artifacts and signal noise, which may create the potential for erroneous or inconsistent imaging values. It is desirable to eliminate or mitigate sound artifacts and signal noise from RF pulses on acoustic receivers in order to processes the valued data. There exists a need to mitigate the impact of RF pulses on acoustic receivers, which can result in cleaner signal data that is used to create imaging values.

In one embodiment, a thermoacoustic probe comprises: a radio-frequency applicator comprising a waveguide with a radio-frequency source, radio-frequency applicator sides, and an exit window; a thermoacoustic transducer comprising a signal cable, thermoacoustic transducer sides, and a piezoelectric front face; a housing configured to contain the radio-frequency applicator and thermoacoustic transducer, wherein the housing enables the exit window and front face to be held flush with respect to each other; a first acoustic absorbing material placed between the radio-frequency applicator and the thermoacoustic transducer, between the radio-frequency applicator and the housing, and between the thermoacoustic transducer and the housing; and a second acoustic absorbing material injected between the radio-frequency applicator and the thermoacoustic transducer, between the radio-frequency applicator and the housing, and between the thermoacoustic transducer and the housing, wherein the first acoustic absorbing material and the second acoustic absorbing material are combined to form a sleeve covering the radio-frequency applicator sides and the thermoacoustic transducer sides.

In one configuration, second acoustic absorbing material forms a sleeve, wherein the exit window and the piezoelectric front face protrude at a proximal end of the sleeve, and further wherein a radio-frequency source and a signal cable protrude from a distal end of the sleeve.

In one configuration, the first acoustic absorbing material is cork.

In one configuration, the second acoustic absorbing material is foam.

In another embodiment, a thermoacoustic probe comprises a housing configured to contain a radio-frequency applicator and a thermoacoustic transducer, wherein the housing enables an exit window of the radio-frequency applicator and a front face of the thermoacoustic transducer to be co-planar with respect to each other; a first acoustic absorbing material disposed between the radio-frequency applicator and the thermoacoustic transducer, between the radio-frequency applicator and the housing, and between the thermoacoustic transducer and the housing; and a second acoustic absorbing material injected between the radio-frequency applicator and the thermoacoustic transducer, between the radio-frequency applicator and the housing, and between the thermoacoustic transducer and the housing.

In yet another embodiment, a thermoacoustic probe comprises a housing configured to contain a radio-frequency applicator and a thermoacoustic transducer, wherein the housing enables an exit window of the radio-frequency applicator and a front face of the thermoacoustic transducer to be co-planar with respect to each other; and an acoustic absorbing material injected between the radio-frequency applicator and the thermoacoustic transducer, between the radio-frequency applicator and the housing, and between the thermoacoustic transducer and the housing.

In another embodiment, a process for manufacturing a thermoacoustic probe comprises positioning a radio-frequency applicator in a housing; positioning a thermoacoustic transducer in the housing; inserting a first acoustic absorbing material into a gap between the radio-frequency applicator and the thermoacoustic transducer, between the radio-frequency applicator and the housing, and between the thermoacoustic transducer and the housing; and injecting a second acoustic absorbing material into the gap between the radio-frequency applicator and the thermoacoustic transducer, between the radio-frequency applicator and the housing, and between the thermoacoustic transducer and the housing.

It should be appreciated that this Summary is provided to introduce a selection of concepts in a simplified form that are further described below in the Detailed Description. This Summary is not intended to be used to limit the scope of the claimed subject matter.

BRIEF DESCRIPTION OF THE DRAWINGS

Embodiments will now be described more fully with reference to the accompanying drawings in which.

DETAILED DESCRIPTION OF THE EMBODIMENTS

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientations depicted in the figures.

The embodiments herein describe an acoustically isolated thermoacoustic imaging probe and process of manufacture.

In one embodiment, the RF applicator has a frequency between about 10 MHz and 100 GHz and has a pulse duration between about 0.1 nanoseconds and 10 microseconds.

Figure 1A:
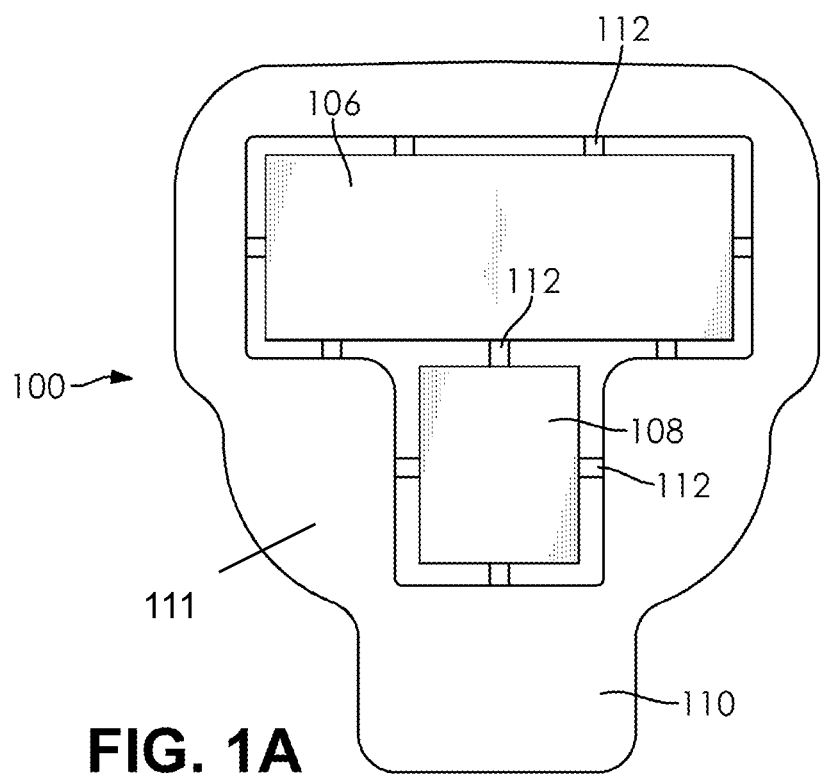
FIG. 1A shows a front view of a radio-frequency applicator and a thermoacoustic transducer mounted in a housing with cork pieces holding the radio-frequency applicator and the thermoacoustic transducer in place, according to an embodiment.
Figure 1B:
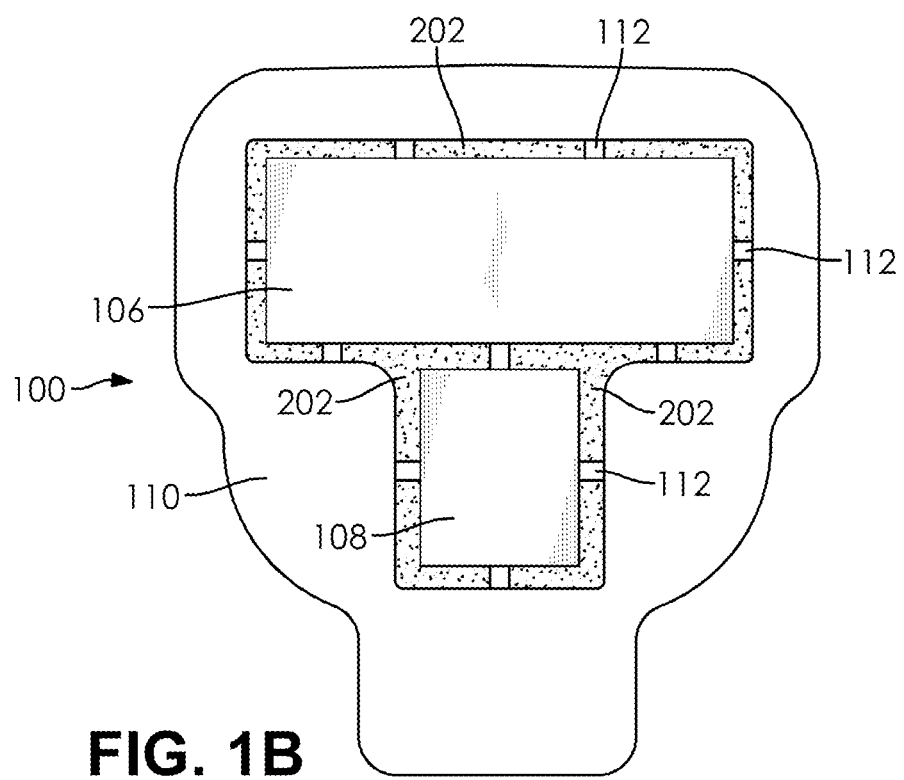
FIG. 1B shows a front view of a radio-frequency applicator and a thermoacoustic transducer mounted in a housing with cork pieces and foam holding the radio-frequency applicator and the thermoacoustic transducer in place, according to an embodiment.

FIGS. 1A and 1B show a front-view of a housing 110 of a thermoacoustic imaging probe 100 having a radio-frequency applicator 106 and a thermoacoustic transducer 108 mounted in a housing 110, according to an embodiment. The radio-frequency applicator 106 has a waveguide with a radio-frequency source, radio-frequency applicator sides, and an exit window. The thermoacoustic transducer 108 has a signal cable, thermoacoustic transducer sides, and a piezoelectric (e.g., lead zirconate titanate (PZT), polymer vinylidine fluoride (PVDF)) front face. The signal cable can connect to an imaging assembly that receives output signals from the imaging probe or for charging a battery power source. In FIG. 1A, a first acoustic absorbing material 112 (an acoustic spacer, such as cork) is disposed between the radio-frequency applicator 106, the thermoacoustic transducer 108, and the housing 110. The acoustic spacer 112 holds the radio-frequency applicator 106 and the thermoacoustic transducer 108 in position prior to the addition of a second acoustic absorbing material 202 (not shown in FIG. 1A). The acoustic spacer 112 can provide sufficient force to hold the radio-frequency applicator 106 and the thermoacoustic transducer 108 in place within the housing. The housing 110 has a planar surface 111 that allows exposure of the exit window of the radio-frequency applicator 106 and piezoelectric front face of the thermoacoustic transducer 108, which are positioned to be co-planar with respect to each other and the surface of the housing 110. The acoustic spacer 112 may be positioned near the surface 111, but is not required to be co-planar with the surface 111.

The acoustic spacer 112 is configured to isolate the radio-frequency applicator 106 from the thermoacoustic transducer 108 and the electronics (not shown) in the housing 110. For example, the acoustic spacer may be configured to scatter or reflect the signal. The first acoustic absorbing material of the acoustic spacer 112 can cause an acoustic impedance m is-match (e.g., a speed of sound m is-match, density mis-match, or both), elastic scattering (e.g., acoustic waves spread out), inelastic scattering (e.g., energy lost in the form of heat), or visco-elastic (e.g., vibration energy is converted to heat in the material deformation process). In some embodiments, it may be desirable for the first acoustic absorbing material to have a density of less than about 1 $g/cm^3$, less than about 0.5 $g/cm^3$, or less than about 0.25 $g/cm^3$. In some embodiments, it may be desirable for the first acoustic absorbing material to have a cell size of about 20 to 60 μm, about 30 to 55 μm, or about 35 to 50 μm. In the example described herein, the first acoustic absorbing material is cork, though it is intended that other acoustic absorbing materials consistent with this disclosure may be utilized. Other acoustic absorbing materials can include ester foams, ether foams, viscoelastic foams, high resiliency foams, and the like.

In FIG. 1B, the second acoustic absorbing material 202 (e.g., polyurethane foam) is shown as sprayed, injected, or otherwise filled between the radio-frequency applicator 106, thermoacoustic transducer 108, and housing 110. As shown in FIG. 1B, the acoustic spacer 112 remains after applying the foam 202.

The second acoustic absorbing material is configured to isolate the radio-frequency applicator 106 from the thermoacoustic transducer 108 and the electronics (not shown) in the housing 110. For example, the second acoustic absorbing material may be configured to scatter or reflect the signal. The second acoustic absorbing material can cause an acoustic impedance m is-match (e.g., a speed of sound mis-match, density mis-match, or both), elastic scattering (e.g., acoustic waves spread out), inelastic scattering (e.g., energy lost in the form of heat), or visco-elastic (e.g., vibration energy is converted to heat in the material deformation process). In some embodiments, it may be desirable for the second acoustic absorbing material to have a density of less than about 1 $g/cm^3$, less than about 0.5 $g/cm^3$, or less than about 0.25 $g/cm^3$. In some embodiments, it may be desirable for the second acoustic absorbing material to have a cell size of about 150 to 400 μm, about 200 to 350 μm, or about 250 to 350 μm. In the example described herein, the second acoustic absorbing material is a polyurethane foam, though it is intended that other acoustic absorbing materials consistent with this disclosure may be utilized. Other acoustic absorbing materials can include styrene-acrylonitrile foam and the like.

Figure 2A:
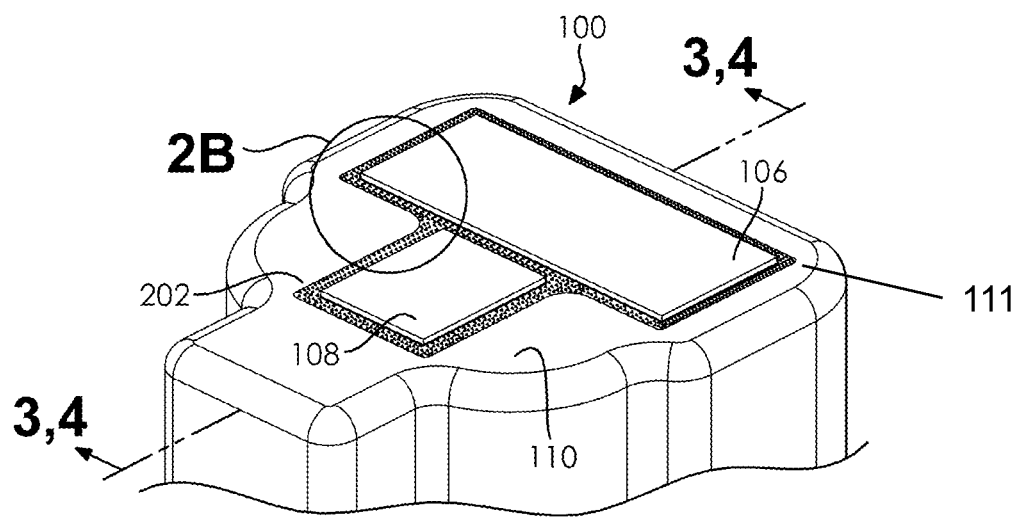
FIGS. 2A and 2B show a perspective view of a radio-frequency applicator and a thermoacoustic transducer mounted in a housing with cork pieces and foam holding the radio-frequency applicator and the thermoacoustic transducer in place, according to an embodiment.
Figure 2B:
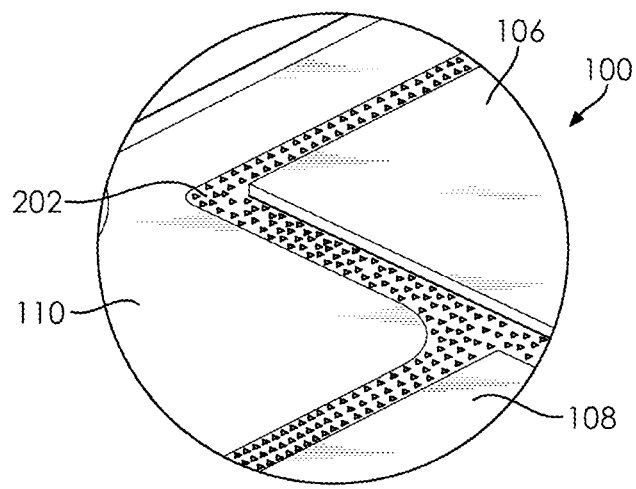

FIG. 2A shows a perspective view of the housing 110, according to an embodiment. FIG. 2B shows an enhanced view of a portion of the housing 110 shown in FIG. 2A, according to an embodiment. As shown, the foam 202 is positioned between the radio-frequency applicator 106 and the thermoacoustic transducer 108, and the foam 202 can hold the radio-frequency applicator 106 and the thermoacoustic transducer 108 in place within the housing 110.

Figure 3:
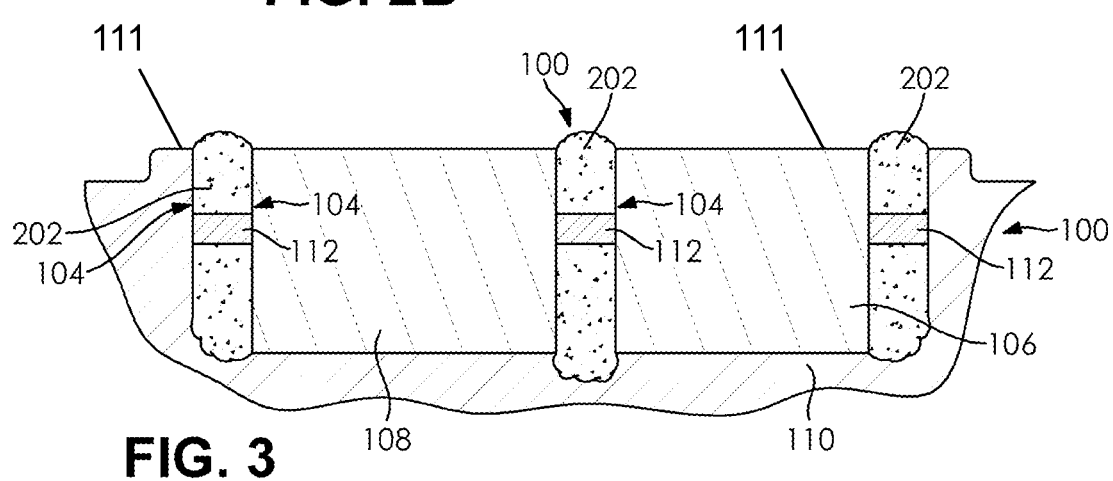
FIG. 3 shows a cross-sectional view of a radio-frequency applicator and a thermoacoustic transducer mounted in a housing with cork pieces and foam holding the radio-frequency applicator and the thermoacoustic transducer in place, according to an embodiment.

FIG. 3 shows a cross-sectional view of a housing 110 along a line 3-3 in FIG. 2A. As shown, the radio-frequency applicator 106 and the thermoacoustic transducer 108 are mounted in the housing 110 with acoustic spacers 112 and foam 202 holding the radio-frequency applicator 106 and the thermoacoustic transducer 108 in place. The foam 202 injected into the housing 110 forms a sleeve 104 around the radio-frequency applicator 106 and the thermoacoustic transducer 108.

The sleeve 104 fills the void between the radio-frequency applicator 106, the thermoacoustic transducer 108, and the housing 110, such that the sleeve 104 covers the sides of the radio-frequency applicator 106 and the thermoacoustic transducer 108, but allows the exposure of the exit window of the radio-frequency applicator 106 and the piezoelectric front face of the thermoacoustic transducer 108 at surface 111. A proximal end of the sleeve 104 can extend to the piezoelectric front face and the exit window. A distal end of the sleeve can extend to the signal cable and radio-frequency source (not shown). In the example configuration, the signal cable and radio-frequency source protrude from the distal end of the sleeve 104.

The applied foam 202 fills the empty space (air gaps) within the housing around the cork spacers 112, which remain in place while the foam 202 is injected and solidifies. The foam 202 may extend beyond the surface 111, as show in FIG. 3. This excess foam may be later removed.

Figure 4:
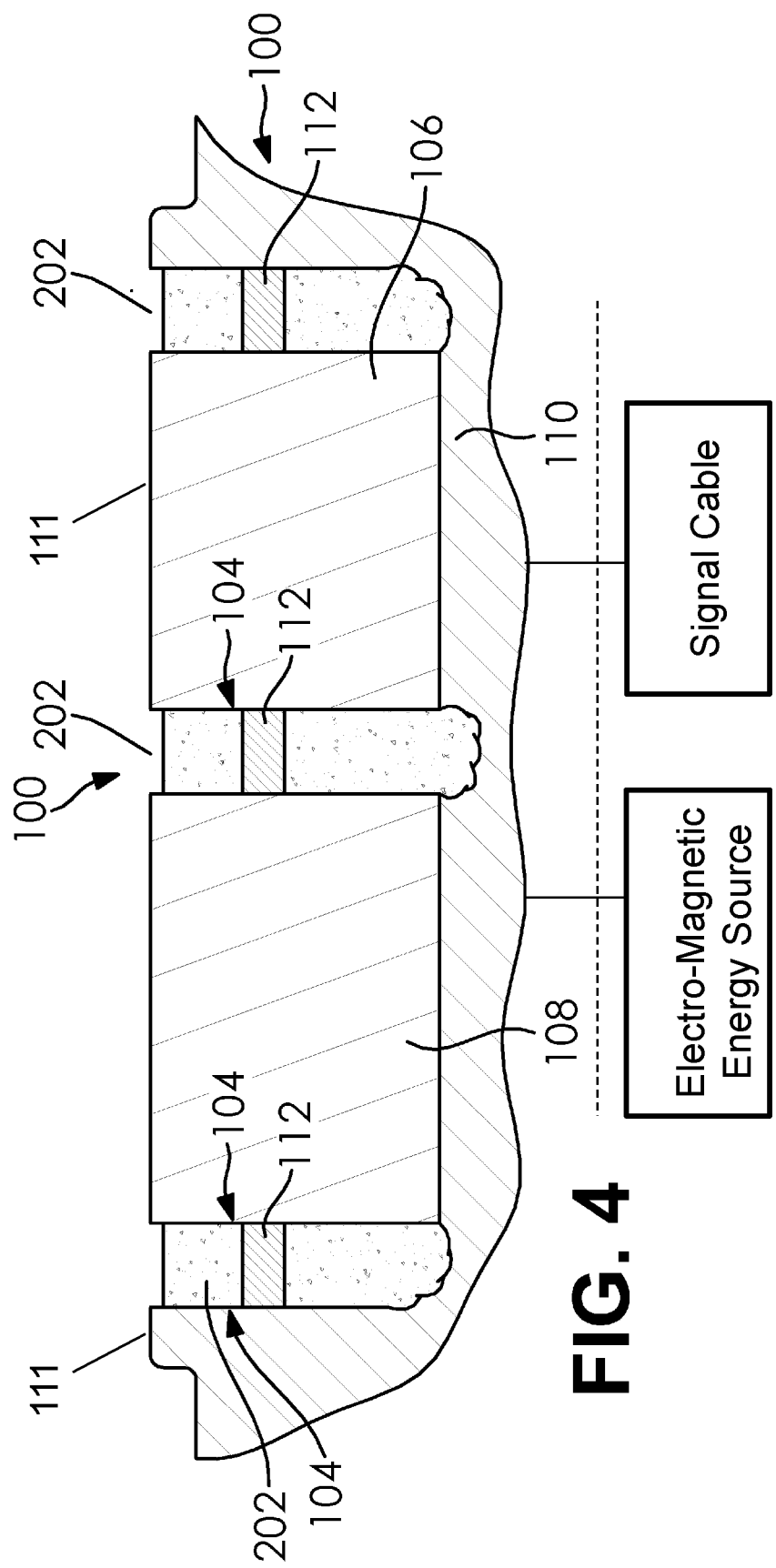
FIG. 4 shows a cross-sectional view of a housing, according to an embodiment.

FIG. 4 shows a cross-sectional view of a housing 100 along a line 4-4 in FIG. 2A. As shown, the radio-frequency applicator 106 and the thermoacoustic transducer 108 are mounted in the housing 110 with acoustic spacers 112 and foam 202 holding the radio-frequency applicator 106 and the thermoacoustic transducer 108 in place, and excess foam 202 extending beyond surface 111 has been removed. The resulting foam in sleeve 104 may be recessed from the surface 111. The piezoelectric front face and the exit window can protrude from the proximal end of the sleeve 104, particularly once the excess foam 202 has been removed.

Figure 5:
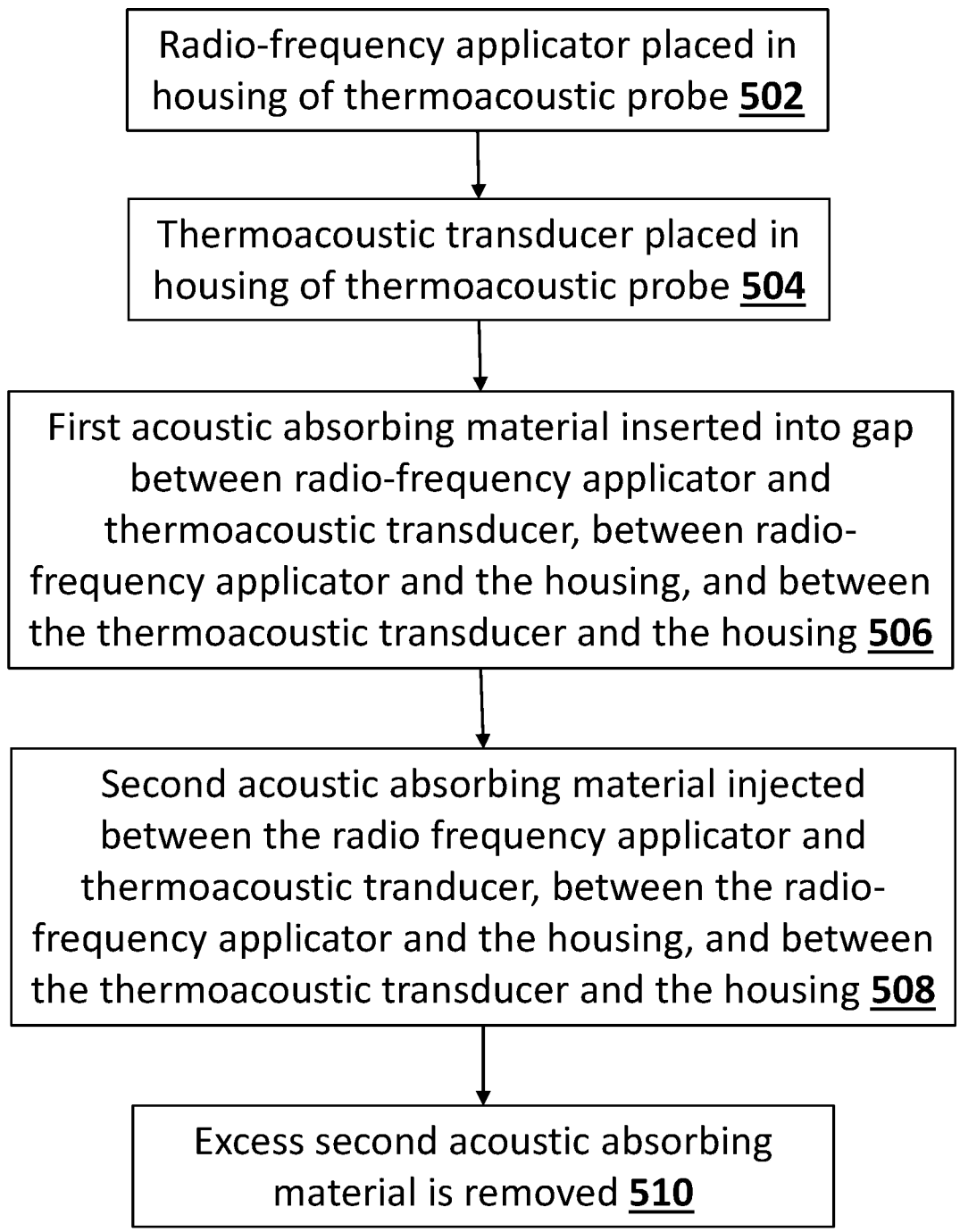
FIG. 5 shows the steps in a process of manufacturing an acoustically isolated thermoacoustic imaging probe, according to an embodiment.

FIG. 5 shows the steps in a process of manufacturing an acoustically isolated thermoacoustic imaging probe. Embodiments may include additional, fewer, or different operations than those described in the method shown in FIG. 5. It should be appreciated that the various operations of this example method can be adapted to various thermoacoustic imaging probe configurations.

In step 502, a radio-frequency applicator is placed in a housing of a thermoacoustic imaging probe. When placed in the housing, a gap exists between the radio-frequency applicator and the housing.

In step 504, a thermoacoustic transducer is placed in the housing of the thermoacoustic imaging probe. Although this example recites placing the radio-frequency applicator in the housing before the thermoacoustic transducer, the thermoacoustic transducer may be placed first or simultaneously with the radio-frequency applicator. The thermoacoustic transducer and the radio-frequency applicator are positioned in the housing such that an exit window and front face are flush with respect to each other. When placed in the housing, a gap exists between the thermoacoustic transducer and the housing, and a gap exists between the thermoacoustic transducer and the radio-frequency applicator.

In step 506, a first acoustic absorbing material (e.g., acoustic spacer) is inserted in the gap between the radio-frequency applicator and the thermoacoustic transducer, between the radio-frequency applicator and the housing, and between the thermoacoustic transducer and the housing. The first acoustic absorbing material may act as a shim to maintain the position of the thermoacoustic transducer and the radio-frequency applicator. The first acoustic absorbing material is placed in the gap below a surface defined by the housing, an exit window of the radio-frequency applicator, and a piezoelectric front face of the thermoacoustic transducer. Additionally or alternatively, screws and/or hot melt adhesive (also known as hot glue) may be used to temporarily align the thermoacoustic transducer, radio-frequency applicator, and housing. Alternatively, in a configuration where the thermoacoustic transducer and radio-frequency applicator can maintain a position in a housing with a consistently-sized gap around the exit window and the front face, then step 506 may be optional.

In step 508, a second acoustic absorbing material is injected between the radio-frequency applicator and the thermoacoustic transducer, between the radio-frequency applicator and the housing, and between the thermoacoustic transducer and the housing. The second acoustic absorbing material fills the gap around the first acoustic absorbing material. The second acoustic absorbing material can also cover the first acoustic absorbing material such that a view of the surface shows only the second acoustic absorbing material, and the first acoustic absorbing material is no longer visible.

In step 510, excess second acoustic absorbing material is removed. The excess second acoustic absorbing material may be removed using tweezers, a scalpel, a scraping tool, or the like. In one example, the acoustic absorbing material is removed to approximately 1 mm below the surface having the exit window of the radio-frequency applicator and the piezoelectric front face of the thermoacoustic transducer. The acoustic absorbing material may be covered in silicone (e.g., room temperature vulcanizing silicone), and excess silicone above the surface may be removed.

Although embodiments have been described above with reference to the accompanying drawings, those of skill in the art will appreciate that variations and modifications may be made without departing from the scope thereof as defined by the appended claims.

What is claimed is:
1. A thermoacoustic probe comprising:
    a housing configured to contain an electromagnetic energy (EM) applicator and a thermoacoustic transducer, wherein the housing enables an exit window of the EM applicator and a front face of the thermoacoustic transducer to be substantially co-planar with respect to each other;
    a first acoustic absorbing material disposed as spacers between the EM applicator and the thermoacoustic transducer, between the EM applicator and the housing, and between the thermoacoustic transducer and the housing; and
    a second acoustic absorbing material injected or sprayed into a gap between the EM applicator and the thermoa- coustic transducer, between the EM applicator and the housing, and between the thermoacoustic transducer and the housing, wherein the second acoustic absorbing material forms a sleeve, and further wherein a proximal end of the sleeve extends to the exit window and the front face.

2. The thermoacoustic probe of claim 1, wherein the second acoustic absorbing material substantially covers a side of the EM applicator and a side of the thermoacoustic transducer.

3. The thermoacoustic probe of claim 2, wherein the first acoustic absorbing material is cork.

4. The thermoacoustic probe of claim 2, wherein the second acoustic absorbing material is foam.

5. The thermoacoustic probe of claim 1, wherein a distal end of the sleeve extends to an EM source and a signal cable.

6. The thermoacoustic probe of claim 5, wherein the exit window and the front face protrude from the sleeve.

7. The thermoacoustic probe of claim 5, wherein the EM source and the signal cable protrude from the sleeve.

8. The thermoacoustic probe of claim 1, wherein the second acoustic absorbing material covers the first acoustic absorbing material.

9. The thermoacoustic probe of claim 1, wherein the EM applicator is a radio-frequency applicator.

10. The thermoacoustic probe of claim 1, wherein the front face of the thermoacoustic transducer is a piezoelectric front face.

11. A process for manufacturing a thermoacoustic probe, the process comprising:

positioning an electromagnetic energy (EM) applicator in a housing;

positioning a thermoacoustic transducer in the housing;

inserting a first acoustic absorbing material into a gap as spacers between the EM applicator and the thermoacoustic transducer, between the EM applicator and the housing, and between the thermoacoustic transducer and the housing; and injecting or spraying a second acoustic absorbing material into the gap between the EM applicator and the thermoacoustic transducer, between the EM applicator and the housing, and between the thermoacoustic transducer and the housing, wherein the second acoustic absorbing material forms a sleeve, and further wherein a proximal end of the sleeve extends towards an exit window of the EM applicator and a front face of the thermoacoustic transducer.

12. The process of claim 11, further comprising removing excess second acoustic absorbing material.

13. The process of claim 11, wherein the second acoustic absorbing material covers the first acoustic absorbing material.

14. The process of claim 11, wherein the first acoustic absorbing material is positioned in the gap below a surface defined by the housing, the exit window, and the front face.

15. The process of claim 14, further comprising removing excess second acoustic absorbing material until the second acoustic absorbing material is below the surface.

16. The process of claim 11, wherein a distal end of the sleeve extends to an EM source and a signal cable.

17. The process of claim 16, wherein the EM source and the signal cable protrude from the sleeve.

18. The process of claim 11, wherein the first acoustic absorbing material is cork, and wherein the second acoustic absorbing material is foam.

19. The process of claim 11, wherein the EM applicator is a radio-frequency applicator.

20. The process of claim 11, wherein the front face of the thermoacoustic transducer is a piezoelectric front face.

* * * * *